(12) United States Patent
Kobayashi et al.

(10) Patent No.: US 8,970,686 B2
(45) Date of Patent: Mar. 3, 2015

(54) ELECTRONIC ENDOSCOPIC APPARATUS

(75) Inventors: Naruyasu Kobayashi, Kawasaki (JP); Kaoru Kotoda, Tokyo (JP); Hisashi Nishimura, Tokyo (JP); Motoo Azuma, Tokorozawa (JP); Kazuhiro Takizawa, Tokyo (JP); Takayuki Sato, Tokyo (JP); Satoshi Tanaka, Tokyo (JP)

(73) Assignee: Olympus Corporation, Tokyo (JP)

( * ) Notice: Subject to any disclaimer, the term of this patent is extended or adjusted under 35 U.S.C. 154(b) by 343 days.

(21) Appl. No.: 13/547,711

(22) Filed: Jul. 12, 2012

(65) Prior Publication Data

US 2013/0016199 A1     Jan. 17, 2013

(30) Foreign Application Priority Data

Jul. 15, 2011   (JP) ................. 2011-156635

(51) Int. Cl.
| | | |
|---|---|---|
| *H04N 7/18* | (2006.01) | |
| *H04N 5/06* | (2006.01) | |
| *A61B 1/00* | (2006.01) | |
| *A61B 1/045* | (2006.01) | |
| *G09G 5/12* | (2006.01) | |
| *G09G 5/00* | (2006.01) | |

(52) U.S. Cl.
CPC ............. *A61B 1/00006* (2013.01); *A61B 1/045* (2013.01); *G09G 5/12* (2013.01); *G09G 2380/08* (2013.01); *G09G 5/005* (2013.01); *G09G 2340/0435* (2013.01)
USPC .................. 348/65; 348/64; 348/72; 348/61; 600/109; 600/101

(58) Field of Classification Search
USPC ...................... 348/65, 64, 72, 61, 69, 211.14; 600/109, 101
See application file for complete search history.

(56) References Cited

U.S. PATENT DOCUMENTS

| | | | |
|---|---|---|---|
| 7,855,727 B2 * | 12/2010 | Adler et al. ............... | 348/65 |
| 2006/0055793 A1 | 3/2006 | Adler et al. | |
| 2007/0139521 A1 * | 6/2007 | Takahashi .............. | 348/65 |

FOREIGN PATENT DOCUMENTS

JP       2001-275956 A       10/2001

OTHER PUBLICATIONS

Extended European Search Report dated Nov. 8, 2012, issued in corresponding European patent application No. 12005140.4.

* cited by examiner

*Primary Examiner* — Jefferey Harold
*Assistant Examiner* — Jean W Desir
(74) *Attorney, Agent, or Firm* — Westerman, Hattori, Daniels & Adrian, LLP

(57) ABSTRACT

An electronic endoscopic apparatus includes an endoscopic scope and an image processing processor. The endoscopic scope includes a solid-state imaging device, an imaging-side multiplying unit, and an imaging synchronization signal generating unit. The image processing processor includes a display clock generating unit, a monitor synchronization signal generating unit, a master imaging clock generating unit, a processor-side multiplying/dividing unit, a phase-comparison oscillation control unit, and a display timing adjustment unit.

10 Claims, 5 Drawing Sheets

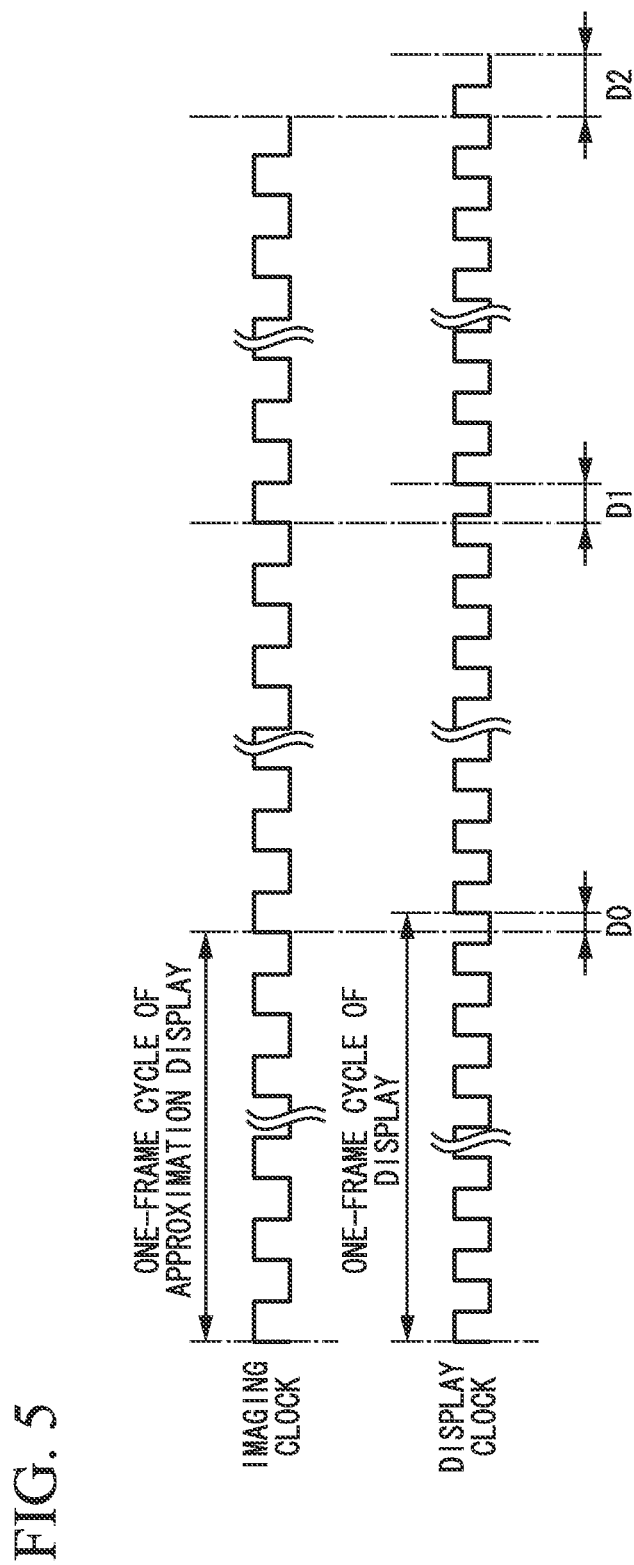

ELECTRONIC ENDOSCOPIC APPARATUS

BACKGROUND OF THE INVENTION

1. Field of the Invention

The present invention relates to an electronic endoscopic apparatus including an endoscopic scope for mounting a slid-state imaging device and an image processing processor for executing predetermined image processing on an image signal from the endoscopic scope.

Priority is claimed on Japanese Patent Application No. 2011-156635, filed on Jul. 15, 2011, the content of which is incorporated herein by reference.

2. Description of Related Art

In recent years, advancements in semiconductor technology are making it possible to increase the pixel density of solid-state imaging devices, such as charge coupled devices (CCD) and complementary metal-oxide semiconductor (CMOS) sensors. An electronic endoscope for mounting a solid-state imaging device is not exempt from this trend, and electronic endoscopes with higher precision are being developed.

However, as the pixel density of solid-state imaging devices increases, so does the frequency of the clock signal needed for the image processing. For example, the electronic endoscope has a structure wherein there is some distance between the distal-end part of the endoscopic scope that the imaging element is mounted on and the image processing processor that performs the image processing, making signal deterioration likely on the transmission line between the endoscopic scope and the image processing processor. When the frequency of signals transmitted between the endoscopic scope and the image processing processor increases, signal deterioration is even greater. Leakage of electromagnetic waves due to the flow of high-frequency signals along the transmission line also becomes more noticeable.

As a method of solving such problems, Japanese Unexamined Patent Application, First Publication No. 2001-275956 proposes an electronic endoscopic apparatus. In this electronic endoscopic apparatus, a smoothing circuit is inserted into the output unit of an electronic endoscope, and suppresses high-frequency noise emitted between the electronic endoscope and a processor device.

However, Japanese Unexamined Patent Application, First Publication No. 2001-275956 does not disclose the perspective of synchronization between the endoscopic scope and a monitor. Since solid-state imaging devices are mounted on the endoscopic scope at various angles of view according to the observation target and the intended purpose, the operating frequency and the angle of view are different for each endoscopic scope. Therefore, to display the image taken by the endoscopic scope, the frequency should be converted according to the synchronization signal of the monitor.

However, depending on the relationship between the clock for display and the clock for imaging, the cycle of the endoscopic scope for taking an image of one frame will be slightly different from the cycle of the monitor for displaying an image of one frame, deviation between the phase of the endoscopic scope and the phase of the monitor is gradually increasing. If the deviation between the phase of the endoscopic scope and the phase of the monitor exceeds the time of one frame, the phenomena known as 'passing' or 'frame dropping' occur.

FIG. 5 is a diagram of the relationship between a one-frame cycle taking an imaging clock as a reference, and a one-frame cycle taking a display clock as a reference. As shown in FIG. 5, there is a slight difference between the one-frame cycle taking an imaging clock as a reference and the one-frame cycle taking a display clock as a reference, and the deviation (D0, D1, D2) between the one-frame cycles is increasing over time.

Meanwhile, monitor is becoming a high-speed as it is becoming a high definition, and the input of a signal to the monitor must satisfy a strict timing standard. Even if the one-frame cycles of imaging and display can be completely matched, when a synchronization signal for display is generated by taking as a reference the clock on the endoscopic scope side that is not compliant with television standards, there is a possibility that an accurate display cannot be achieved on the monitor.

SUMMARY OF THE INVENTION

According to a first aspect of the present invention, an electronic endoscopic apparatus includes an endoscopic scope and an image processing processor. The endoscopic scope includes a solid-state imaging device, an imaging-side multiplying unit, and an imaging synchronization signal generating unit. The image processing processor includes a display clock generating unit, a monitor synchronization signal generating unit, a master imaging clock generating unit, a processor-side multiplying/dividing unit, a phase-comparison oscillation control unit, and a display timing adjustment unit.

The solid-state imaging device is configured to convert optical information to an electrical signal, and is configured to output the electrical signal as an image signal. The imaging-side multiplying unit is configured to generate a scope-side multiplication clock by multiplying a transmission imaging clock input from the image processing processor. The imaging synchronization signal generating unit is configured to generate an imaging synchronization signal for driving the solid-state imaging device from the scope-side multiplication clock.

The display clock generating unit is configured to generate a display clock. The monitor synchronization signal generating unit is configured to generate a monitor synchronization signal based on the display clock. The master imaging clock generating unit is configured to generate a master imaging clock. The processor-side multiplying/dividing unit is configured to generate a process-side imaging clock obtained by converting the master imaging clock, and is configured to generate a transmission imaging clock obtained by converting the master imaging clock. The phase-comparison oscillation control unit is configured to compare the phases of the monitor synchronization signal and the processor-side imaging clock, and is configured to control the oscillation of the master imaging clock generating unit based on the result of that comparison. The display timing adjustment unit is configured to use the imaging synchronization signal, the processor-side imaging clock, the monitor synchronization signal, and the display clock, and is configured to output the image signal in synchrony with the monitor synchronization signal.

According to a second aspect of the present invention, the display timing adjustment unit includes a frame buffer that stores the image signal, a write control unit that, based on the imaging synchronization signal and the processor-side imaging clock, writes the image signal to the frame buffer, and a read control unit that, based on the monitor synchronization signal and the display clock, reads the image signal that was written to the frame buffer.

According to a third aspect of the present invention, the monitor synchronization signal generating unit further adjusts the timing of starting the generation of the monitor synchronization signal, based on the imaging synchronization signal.

According to a fourth aspect of the present invention, the image processing processor includes a plurality of groups of the display clock generating unit, the monitor synchronization signal generating unit, and the display timing adjustment unit. One of the plurality of groups is deemed a master, and groups other than the master are deemed slaves. Each of the slaves further includes a phase-comparison oscillation control unit that compares the phase of the monitor synchronization signal generated by the monitor synchronization signal generating unit of the master with the phase of the display clock generated by the display clock generating unit of the slave, and accordingly controls the oscillation of the display clock generating unit of the slave.

Preferably, the processor-side imaging clock obtained by converting the master imaging clock includes a processor-side imaging clock obtained by multiplying the master imaging clock.

Preferably, the processor-side imaging clock obtained by converting the master imaging clock includes a processor-side imaging clock obtained by dividing the master imaging clock.

Preferably, the processor-side imaging clock obtained by converting the master imaging clock includes a processor-side imaging clock obtained by multiplying and dividing the master imaging clock.

Preferably, the transmission imaging clock obtained by converting the master imaging clock includes a transmission imaging clock obtained by multiplying the master imaging clock.

Preferably, the transmission imaging clock obtained by converting the master imaging clock includes a transmission imaging clock obtained by dividing the master imaging clock.

Preferably, the transmission imaging clock obtained by converting the master imaging clock includes a transmission imaging clock obtained by multiplying and dividing the master imaging clock.

BRIEF DESCRIPTION OF THE DRAWINGS

FIG. 5 is a timing chart for explanation of conventional problems.

DETAILED DESCRIPTION OF INVENTION

Embodiments of the present invention will be explained with reference to the drawings.

First Embodiment

Figure 1:
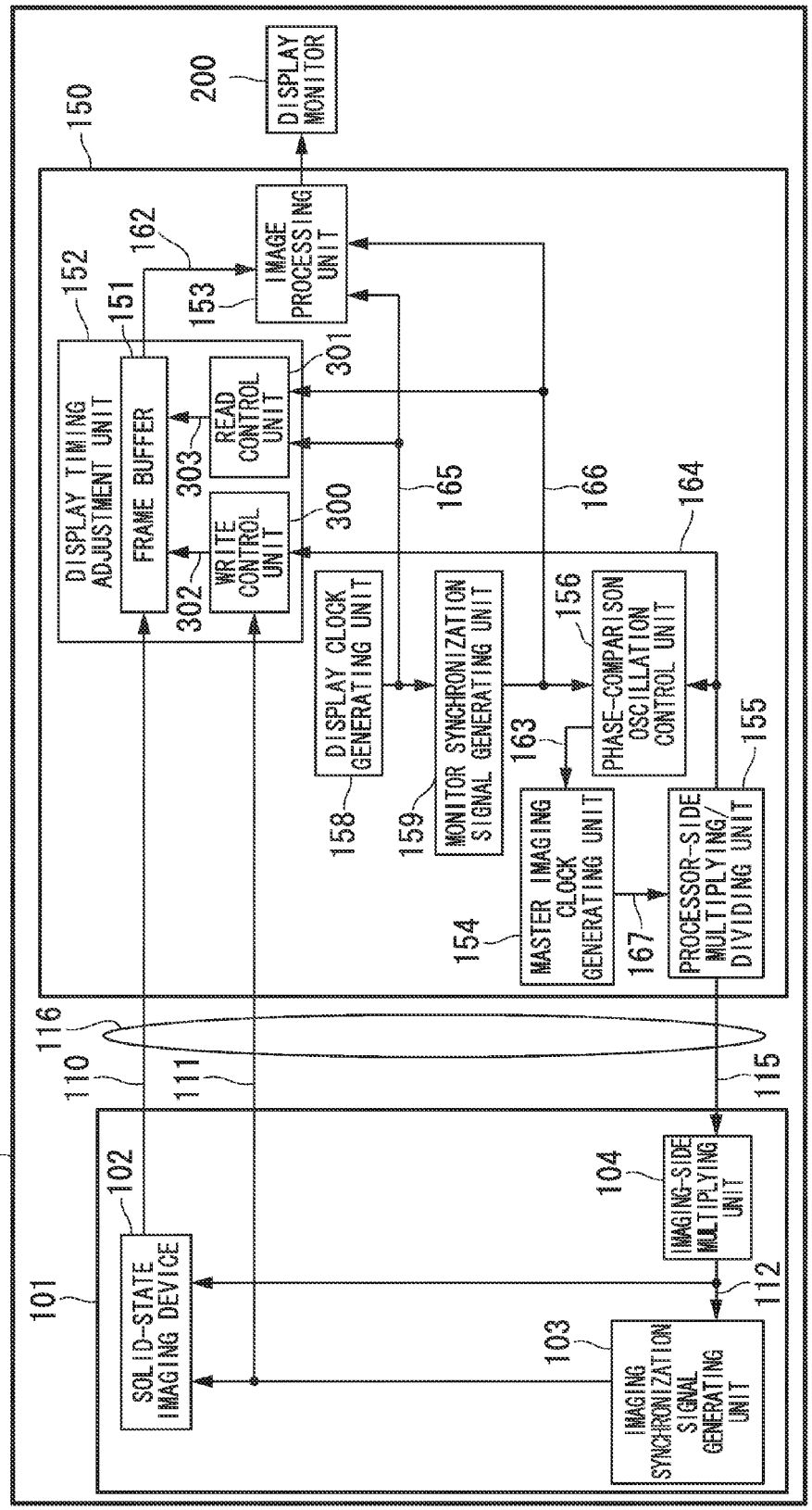
FIG. 1 is a block diagram showing the configuration of an electronic endoscopic apparatus according to a first embodiment of the present invention.

A first embodiment of the present invention will be explained. FIG. 1 is a configuration of an electronic endoscopic apparatus according to the embodiment. An electronic endoscopic apparatus 100 includes an endoscopic scope 101 and an image processing processor 150. The endoscopic scope 101 and the image processing processor 150 are connected by a transmission cable 116.

The image processing processor 150 includes a display timing adjustment unit 152, an image processing unit 153, a master imaging clock generating unit 154, a processor-side multiplying/dividing unit 155, a phase-comparison oscillation control unit 156, a display clock generating unit 158, and a monitor synchronization signal generating unit 159. The endoscopic scope 101 includes a solid-state imaging device 102, an imaging synchronization signal generating unit 103, and an imaging-side multiplying unit 104.

The display clock generating unit 158 generates a display clock 165 for driving the various parts of the display. The display clock 165 generated by the display clock generating unit 158 is output to the monitor synchronization signal generating unit 159, the display timing adjustment unit 152, and the image processing unit 153. The monitor synchronization signal generating unit 159 generates a monitor synchronization signal 166 (display synchronization signal) that is compliant with a television standard for displaying an image on a display monitor 200. The display clock 165 generated by the display clock generating unit 158 is used in generating the monitor synchronization signal 166. The monitor synchronization signal 166 generated by the monitor synchronization signal generating unit 159 is output to the phase-comparison oscillation control unit 156, the display timing adjustment unit 152, and the image processing unit 153.

The master imaging clock generating unit 154 generates a master imaging clock 167 that becomes the source of a signal for driving the solid-state imaging device 102 of the endoscopic scope 101. The processor-side multiplying/dividing unit 155 executes, as appropriate, a process of multiplication only, a process of division only, or a process combining multiplication and division, to the master imaging clock 167 generated by the master imaging clock generating unit 154, and generates a transmission imaging clock 115 and a processor-side imaging clock 164. The transmission imaging clock 115 is transmitted to the endoscopic scope 101. The frequency of the transmission imaging clock 115 is lower than the frequency of the master imaging clock 167 generated by the master imaging clock generating unit 154. The processor-side imaging clock 164 is output to the phase-comparison oscillation control unit 156 and the display timing adjustment unit 152. The frequency of the processor-side imaging clock 164 is higher than the frequency of the master imaging clock 167 generated by the master imaging clock generating unit 154.

The phase-comparison oscillation control unit 156 compares the phases of the monitor synchronization signal 166 and the processor-side imaging clock 164, and, based on the result of that comparison, generates a control signal 163 for controlling the oscillation state of the master imaging clock 167 in the master imaging clock generating unit 154, and outputs it to the master imaging clock generating unit 154. Based on the control signal 163, the master imaging clock generating unit 154 controls the oscillation frequency of the master imaging clock 167. As a result, the frequency of the master imaging clock 167 becomes an integral multiple of the frequency of the monitor synchronization signal 166, and the master imaging clock 167 and the monitor synchronization signal 166 are synchronized.

Since there are oscillators that allow the frequency to be changed arbitrarily in accordance with a control signal from the outside, the master imaging clock generating unit 154 can be mounted using such oscillators.

Figure 2:
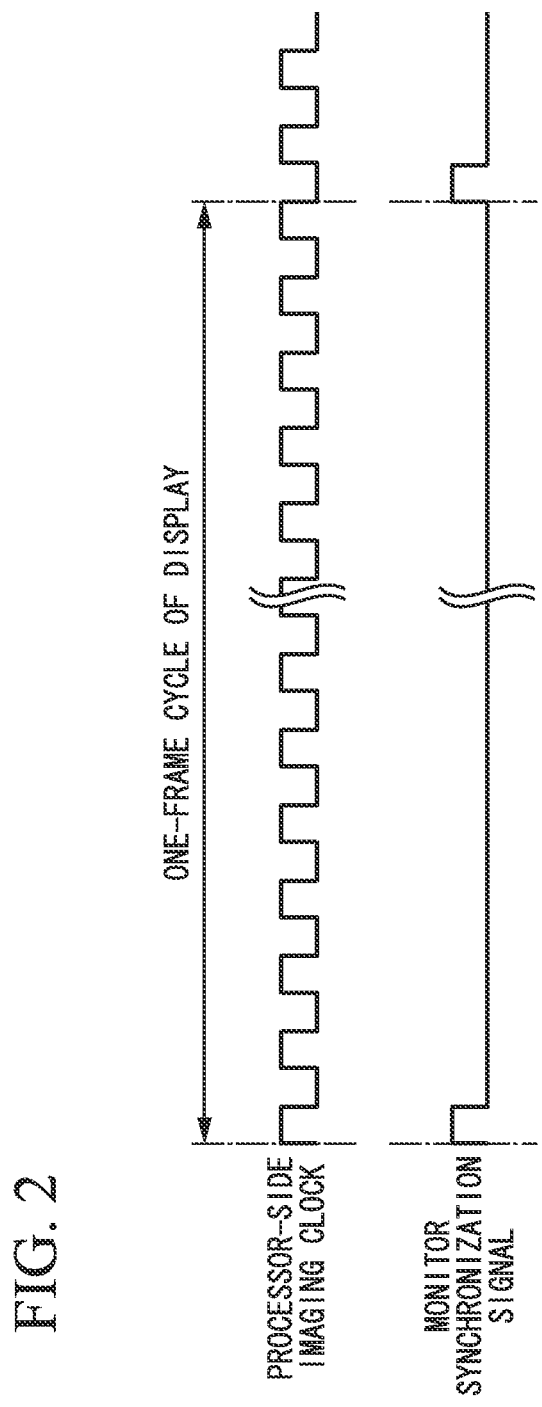
FIG. 2 is a timing chart for explanation of the operation of a phase-comparison oscillation control unit included in an electronic endoscopic apparatus according to a first embodiment of the present invention.

FIG. 2 shows the content of an operation of the phase-comparison oscillation control unit 156. The phase-comparison oscillation control unit 156 compares, for example, the rising edge of the processor-side imaging clock 164 with the rising edge the monitor synchronization signal 166 (a vertical synchronization signal in the example of FIG. 2), and outputs a control signal 163 based on the difference between them to the master imaging clock generating unit 154. Based on the control signal 163, the master imaging clock generating unit 154 controls the frequency of the master imaging clock 167 (i.e. the master imaging clock 167 switches to an oscillating state). Thus the rising edge of the processor-side imaging clock 164 generated by the master imaging clock 167 matches the rising edge of the monitor synchronization signal 166, achieving synchronization between the processor-side imaging clock 164 and the monitor synchronization signal 166. While the example of FIG. 2 uses a vertical synchronization signal in the phase comparison with the processor-side imaging clock 164, a horizontal synchronization signal can be used instead.

After the master imaging clock 167 has been brought into phase with the monitor synchronization signal 166 in this way, it is multiplied and divided by the processor-side multiplying/dividing unit 155 to generate the transmission imaging clock 115 and the processor-side imaging clock 164. The transmission imaging clock 115 is output from the image processing processor 150 to the endoscopic scope 101.

The transmission imaging clock 115 is input to the imaging-side multiplying unit 104 of the endoscopic scope 101 via the transmission cable 116 connecting the endoscopic scope 101 and the image processing processor 150. The imaging-side multiplying unit 104 multiplies the transmission imaging clock 115, and generates an scope-side multiplication clock 112 having the same frequency as the processor-side imaging clock 164. The scope-side multiplication clock 112 generated by the imaging-side multiplying unit 104 is output to the imaging synchronization signal generating unit 103 and the solid-state imaging device 102.

From the scope-side multiplication clock 112, the imaging synchronization signal generating unit 103 generates an imaging synchronization signal 111 for driving the solid-state imaging device 102. The solid-state imaging device 102 is a CMOS sensor. In compliance with the scope-side multiplication clock 112 and the imaging synchronization signal 111, the solid-state imaging device 102 converts the optical information to an electrical signal, and outputs a digital image signal 110. The digital image signal 110 and the imaging synchronization signal 111 are output from the endoscopic scope 101, and are input via the transmission cable 116 to the display timing adjustment unit 152 of the image processing processor 150.

The display timing adjustment unit 152 in the image processing processor 150 uses the processor-side imaging clock 164 and the imaging synchronization signal 111 to receive the digital image signal 110 transmitted from the endoscopic scope 101. The display timing adjustment unit 152 converts the received digital image signal 110 to a digital image signal 162 that is synchronized with the timing of the monitor synchronization signal 166, and outputs to the image processing unit 153. That is, the display timing adjustment unit 152 executes a process (known as a clock transfer) of switching the clock for processing the digital image signal 110 to the display clock 165 from the processor-side imaging clock 164. At this time, the imaging synchronization signal 111 and the monitor synchronization signal 166 are used as signals for indicating the frame start timings of the digital image signals 110 and 162.

More specifically, the display timing adjustment unit 152 executes the following process. The display timing adjustment unit 152 includes a frame buffer 151, a write control unit 300, and a read control unit 301. The write control unit 300 uses the imaging synchronization signal 111 and the processor-side imaging clock 164 to detect the start timing of the frame on the imaging side, and generates a write control signal 302 for controlling the writing of data to the frame buffer 151. Based on the write control signal 302, the frame buffer 151 stores the digital image signal 110.

The read control unit 301 uses the monitor synchronization signal 166 and the display clock 165 to detect the start timing of the frame on the display side, and generates a read control signal 303 for controlling the reading of data from the frame buffer 151. Based on the read control signal 303, the frame buffer 151 outputs the stored digital image signal 110 as a digital image signal 162 to the image processing unit 153. While in the embodiment, the imaging synchronization signal 111, which is the synchronization signal on the imaging side, and the monitor synchronization signal 166, which is the synchronization signal on the display side, are generated at mutually independent timings, deviation between the start timings of the imaging-side and display-side frames can be absorbed by using the frame buffer 151 in performing the process described above.

The image processing unit 153 subjects the digital image signal 162 input from the frame buffer 151 to a predetermined image process for displaying an image using the display clock 165 and the monitor synchronization signal 166. The processed digital image signal 162 is output to the display monitor 200, and used in display an image on the display monitor 200.

As described above, according to the embodiment, the oscillation frequency of the master imaging clock 167 is adjusted taking the monitor synchronization signal 166 as a reference, and the phase of the master imaging clock 167 is matched to that of the monitor synchronization signal 166 (the master imaging clock 167 is synchronized with the monitor synchronization signal 166). By generating the imaging synchronization signal 111 for driving the solid-state imaging device 102 from this synchronized master imaging clock 167, the cycles of the frames on the display side and the imaging side can be matched, making it possible to synchronize the imaging and the display. This can prevent passing of frames due to mismatch between the frame cycles.

Since the display timing adjustment unit 152 can absorb deviation in the start timings of frames on the imaging side and the display side, the imaging synchronization signal generating unit 103 can generate the imaging synchronization signal 111 without relation to the monitor synchronization signal 166. Thus the imaging synchronization signal generating unit 103 can be made simpler, since it need not refer to the monitor synchronization signal 166, and wiring for transmitting synchronization signal need not be provided inside the transmission cable 116. Therefore, the endoscopic scope 101 can be made smaller (narrower). Given that the endoscopic scope is used by inserting it into the human body, this capability to be made narrower is highly advantageous.

The transmission imaging clock 115 is transmitted to the endoscopic scope 101 at a low frequency that is slower than the processor-side imaging clock 164 used in the endoscopic scope 101. It is therefore possible to reduce problems associated with higher speed, such as signal deterioration and the effects of disturbance noise generated when using a high-frequency clock. Moreover, electromagnetic noise can be suppressed.

When the endoscopic scope 101 is replaced with something else, even if the start timing of the frame on the imaging side changes, the start timing of the frame on the display side is the same as it was before the endoscopic scope 101 was replaced, and the synchronization signal output to the display monitor 200 does not change. Therefore, the screen is not disturbed by synchronization loss on the display monitor 200.

The embodiment can be modified in various ways. For example, while the embodiment uses a CMOS sensor as the solid-state imaging device 102, a CCD can be used instead. Also, various types of processing circuits can be mounted on the same chip as the solid-state imaging device 102. Therefore, the circuits of the imaging synchronization signal generating unit 103 and the imaging-side multiplying unit 104 can be mounted on the same chip as the solid-state imaging device 102.

Second Embodiment

Figure 3:
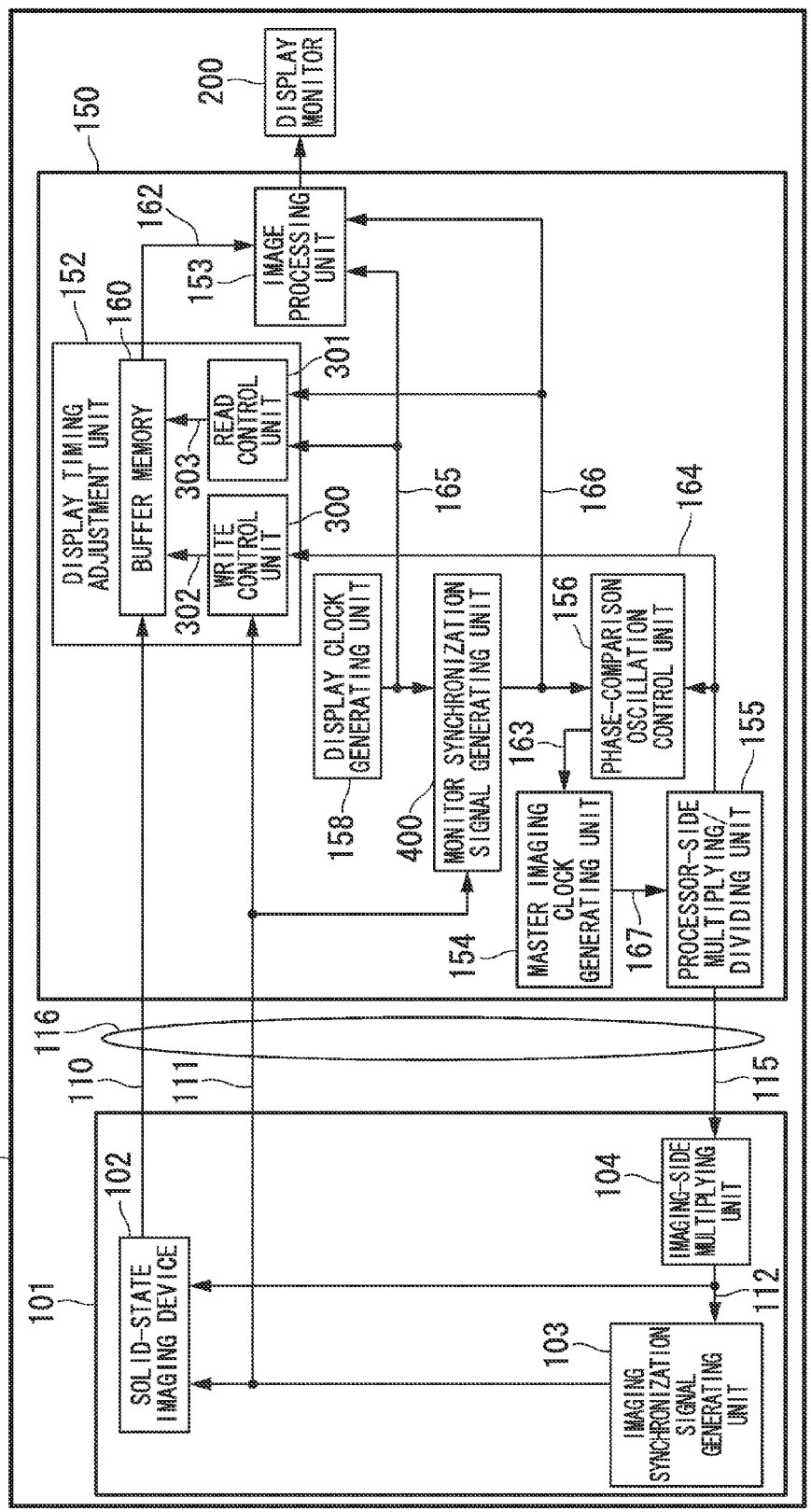
FIG. 3 is a block diagram showing the configuration of an electronic endoscopic apparatus according to a second embodiment of the present invention.

Subsequently, a second embodiment of the present invention will be explained. FIG. 3 is the configuration of an electronic endoscopic apparatus according to the embodiment. In FIG. 3, constituent elements having like functions to those of the first embodiment are designated with like reference codes and are not repetitiously explained.

The embodiment includes a monitor synchronization signal generating unit 400 instead of the monitor synchronization signal generating unit 159 in the first embodiment. The display clock 165 generated by the display clock generating unit 158 and the imaging synchronization signal 111 received from the endoscopic scope 101 are input to the monitor synchronization signal generating unit 400. Based on change in the imaging synchronization signal 111, the monitor synchronization signal generating unit 400 detects that the endoscopic scope 101 has started an imaging process, and simultaneously detects the start timing of the frame on the imaging side. Taking the detected start timing of the frame on the imaging side as a reference, the monitor synchronization signal generating unit 400 starts generating the monitor synchronization signal 166 after a predetermined time has elapsed from that start timing.

Since an electronic endoscopic apparatus 100 according to the embodiment takes the monitor synchronization signal 166 as a reference for the frame cycle, it is preferable not to interfere with the operation of generating the monitor synchronization signal 166 unless absolutely necessary. Therefore, the monitor synchronization signal generating unit 400 adjusts the generation timing of the monitor synchronization signal 166 on the display side at the timing when the switch of the endoscopic scope 101 was detected.

While the first embodiment requires a large memory for timing-adjustment with a capacity of one frame to absorb deviation in the start timings of the frames, in the embodiment, since the monitor synchronization signal generating unit 400 can reduce the deviation width of the start timings of the frames and keep it constant, the memory can be small. Therefore, the display timing adjustment unit 152 of the embodiment includes a buffer memory 160 instead of the frame buffer 151 in the first embodiment.

According to the embodiment, it is possible to match the cycles of frames on the display side and the imaging side, and to maintain synchrony between imaging and display. The monitor synchronization signal generating unit 400 generates the monitor synchronization signal 166 taking the imaging synchronization signal 111 as a reference, whereby the delay time between the imaging and display frames can be adjusted to a constant. Therefore, since it becomes possible to reduce the time difference from the start timing of the imaging-side frame to the start timing of the display-side frame, the buffer capacity needed to adjust the output timing can also be reduced.

The embodiment can be modified in various ways. For example, while the embodiment uses the buffer memory 160, a logical circuit such as a shift register capable of holding several clocks of the digital image signal 110 can be used instead.

Third Embodiment

Figure 4:
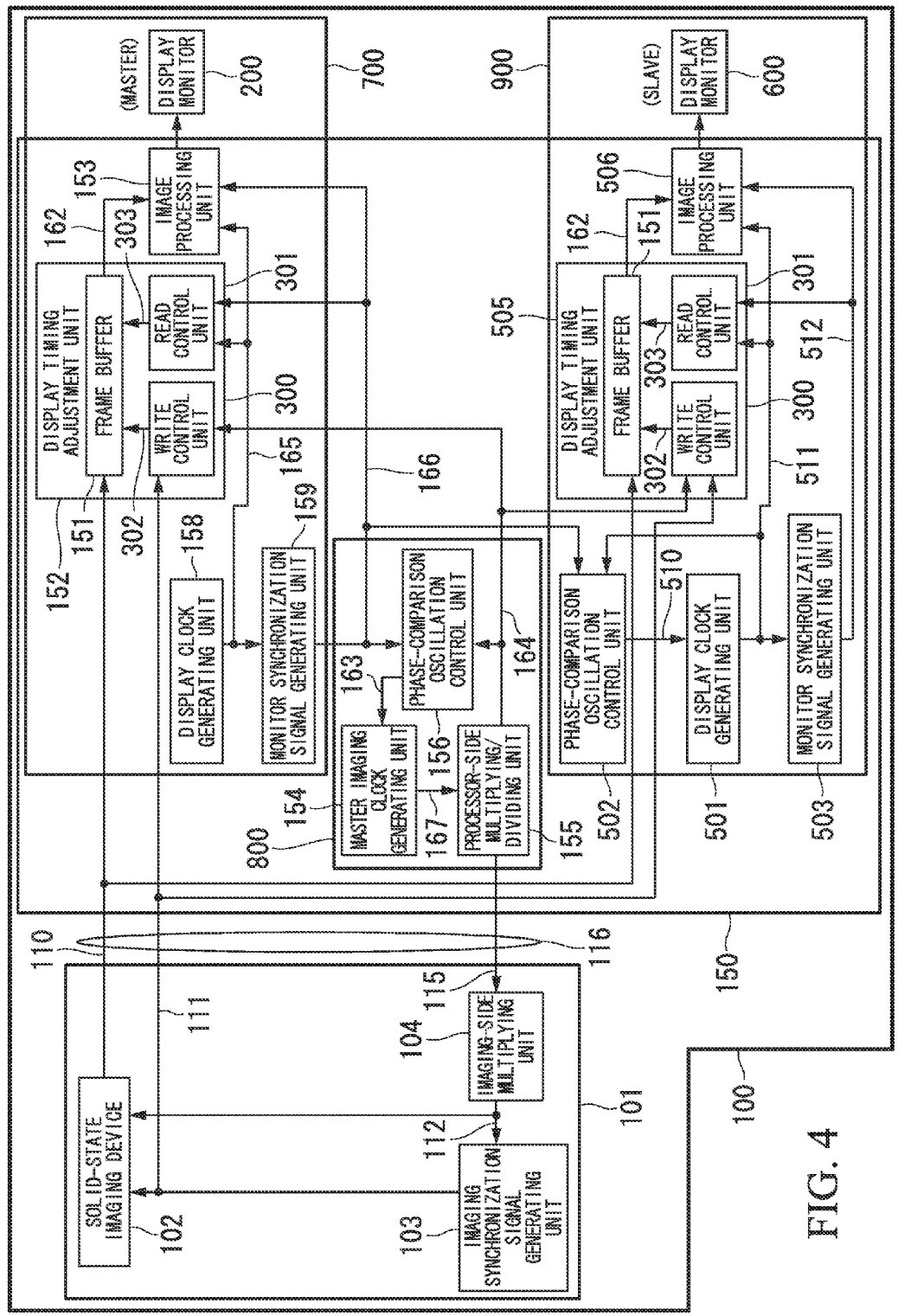
FIG. 4 is a block diagram showing the configuration of an electronic endoscopic apparatus according to a third embodiment of the present invention.

Subsequently, a third embodiment of the present invention will be explained. FIG. 4 is the configuration of an electronic endoscopic apparatus according to the embodiment. In FIG. 4 constituent elements having like functions to those of the first embodiment are designated with like reference codes and are not repetitiously explained.

There are cases where an image captured by a single endoscopic scope is output to a plurality of devices. In some cases, this requires the output of image signals of different standards. For example, there are cases where an image is observed on a high-definition display monitor while being recorded using a standard-definition recording device, etc. In the first embodiment and the second embodiment, deviation between the cycles of the synchronization signals on the display side and the imaging side is avoided. However, when a plurality of display monitors are used simultaneously, if the cycle of the synchronization signal on the imaging side is simply matched to a cycle corresponding to one of the image signals, the frame cycles of the other image signals will not completely match the synchronization signal on the imaging side, leading to a problem of the display being passed.

As an example of differing display standards, a case will be explained where an image is simultaneously displayed on two display monitors, one of which is a high-definition television (HDTV) monitor and the other is a standard-definition television (SDTV) monitor. Usually, image signals of these standards have a matching frame cycle of 59.94 Hz, with a clock frequency of 74.1758 MHz being used for HDTV display, and a clock frequency of 13.5 MHz being used for SDTV display. Unless measures are taken, the degree of precision (error) of the oscillators that generate these clocks will make it impossible to completely match the frame cycle for HDTV display with the frame cycle for SDTV display. Consequently, if only the imaging-side frame cycle is matched with the frame cycle for HDTV display, there will be deviation between the imaging-side frame cycle and the frame cycle for SDTV display, resulting in frame passing in the image display on the SDTV monitor.

The image processing processor 150 of the embodiment is connected to the display monitor 200 and to a display monitor 600. The display standard of the display monitor 600 is different from that of the display monitor 200. Here, a configuration matched with the display standard of the display monitor 200 is deemed a master standard unit 700, and a configuration matched with the display standard of the display monitor 600 is deemed a slave standard unit 900.

The master standard unit 700 includes a display timing adjustment unit 152, an image processing unit 153, a display clock generating unit 158, and a monitor synchronization signal generating unit 159. The slave standard unit 900 includes a display timing adjustment unit 505, an image processing unit 506, a display clock generating unit 501, a phase-comparison oscillation control unit 502, and a monitor synchronization signal generating unit 503. While the master standard unit 700 and the slave standard unit 900 differ in that the slave standard unit 900 includes a phase-comparison oscillation control unit 502, their other constitutive elements have basically similar functions. However, due to differences in the oscillation frequencies of the display clock and the specifications of the synchronization signals in the display standards, their operations are not identical.

A processor-side imaging clock generator 800 includes a master imaging clock generating unit 154, a processor-side multiplying/dividing unit 155, and a phase-comparison oscillation control unit 156, and generates a processor-side imaging clock 164. The processor-side imaging clock 164 generated by the processor-side imaging clock generator 800 is output to the display timing adjustment unit 152 of the master standard unit 700 and the display timing adjustment unit 505 of the slave standard unit 900.

In the slave standard unit 900, the phase-comparison oscillation control unit 502 compares the phase of the monitor synchronization signal 166 generated by the master standard unit 700 with the phase of a display clock 511 generated by the display clock generating unit 501, generates a control signal 510 based on the result of that comparison, and outputs to the display clock generating unit 501. Based on the control signal 510, the display clock generating unit 501 controls the oscillation frequency of the display clock 511. As a result, the phase of the display clock 511 matches the phase of the monitor synchronization signal 166 generated by the master standard unit 700. Based on the display clock 511, the monitor synchronization signal generating unit 503 generates a monitor synchronization signal 512. The generated monitor synchronization signal 512 and the display clock 511 are output to the display timing adjustment unit 505.

As in the first embodiment, the display timing adjustment unit 505 matches the timing of the digital image signal 110 to that of the monitor synchronization signal 512, and outputs it as a digital image signal 162 to the image processing unit 506. The image processing unit 506 subjects the digital image signal 162 input from the display timing adjustment unit 505 to a predetermined image process. The processed digital image signal 162 is output to the display monitor 600, and used in displaying an image on the display monitor 600. While the transmission imaging clock 115 supplied to the imaging side is generated in a manner similar to that of the first embodiment, the monitor synchronization signal 166 is referred to as a reference synchronization signal.

According to the embodiment, the oscillation of the display clock 511 and the master imaging clock 167 is controlled such that they match the phase of the monitor synchronization signal 166 generated by the master standard unit 700, whereby the phases of the clocks used in generating the monitor synchronization signal 512 and the imaging synchronization signal 111 can be matched to the phase of the monitor synchronization signal 166 generated by the master standard unit 700. Therefore, when using image signal standards with the same frame frequency, the frame cycles of all the image signals can be matched completely. Thus, even if images are simultaneously displayed on display monitors with different display standards, there is no passing of frames on the display monitors.

While the embodiment uses two display monitors with different display standards, three or more monitors of different display standards can be used. In that case, one predetermined display standard from the plurality of display standards is used as a master standard and the others are used as slave standards, two or more of the slave standard units 900 in FIG. 4 are provided, and the monitor synchronization signal 166, the imaging synchronization signal 111, the digital image signal 110, and the processor-side imaging clock 164 are input to each of the slave standard units 900.

While embodiments of the invention have been described with reference to the drawings, the specific configurations are not limited to the embodiments described above, and includes various design modifications and the like that do not depart from the main points of the invention.

The invention is not to be considered as being limited by the foregoing description, and is only limited by the scope of the appended claims.

What is claimed is:

1. An electronic endoscopic apparatus comprising:
an endoscopic scope; and
an image processing processor, wherein the endoscopic scope comprises:
a solid-state imaging device is configured to convert optical information to an electrical signal, and is configured to output the electrical signal as an image signal;
an imaging-side multiplying unit is configured to generate a scope-side multiplication clock by multiplying a transmission imaging clock input from the image processing processor; and
an imaging synchronization signal generating unit is configured to generate an imaging synchronization signal for driving the solid-state imaging device from the scope-side multiplication clock;
and the image processing processor comprises:
a display clock generating unit is configured to generate a display clock;
a monitor synchronization signal generating unit is configured to generate a monitor synchronization signal based on the display clock;
a master imaging clock generating unit is configure to generate an master imaging clock;
a processor-side multiplying/dividing unit is configured to generate a process-side imaging clock obtained by converting the master imaging clock, and is configured to generate a transmission imaging clock obtained by converting the master imaging clock;
a phase-comparison oscillation control unit is configured to compare the phases of the monitor synchronization signal and the processor-side imaging clock, and controls the oscillation of the master imaging clock generating unit based on the result of that comparison; and
a display timing adjustment unit is configured to use the imaging synchronization signal, the processor-side imaging clock, the monitor synchronization signal, and the display clock, and is configured to output the image signal in synchrony with the monitor synchronization signal.

2. The electronic endoscopic apparatus according to claim 1, wherein the display timing adjustment unit comprises:
a frame buffer that stores the image signal;
a write control unit that, based on the imaging synchronization signal and the processor-side imaging clock, writes the image signal to the frame buffer; and
a read control unit that, based on the monitor synchronization signal and the display clock, reads the image signal that was written to the frame buffer.

3. The electronic endoscopic apparatus according to claim 1, wherein the monitor synchronization signal generating unit further adjusts the timing of starting the generation of the monitor synchronization signal, based on the imaging synchronization signal.

4. The electronic endoscopic apparatus according to claim 1, wherein the image processing processor comprises a plurality of groups of the display clock generating unit, the monitor synchronization signal generating unit, and the display timing adjustment unit;
    one of the plurality of groups being deemed a master, and groups other than the master being deemed slaves; and
    each of the slaves further comprises a phase-comparison oscillation control unit that compares the phase of the monitor synchronization signal generated by the monitor synchronization signal generating unit of the master with the phase of the display clock generated by the display clock generating unit of the slave, and accordingly controls the oscillation of the display clock generating unit of the slave.

5. The electronic endoscopic apparatus according to claim 1, wherein the processor-side imaging clock obtained by converting the master imaging clock comprises a processor-side imaging clock obtained by multiplying the master imaging clock.

6. The electronic endoscopic apparatus according to claim 1, wherein the processor-side imaging clock obtained by converting the master imaging clock comprises a processor-side imaging clock obtained by dividing the master imaging clock.

7. The electronic endoscopic apparatus according to claim 1, wherein the processor-side imaging clock obtained by converting the master imaging clock comprises a processor-side imaging clock obtained by multiplying and dividing the master imaging clock.

8. The electronic endoscopic apparatus according to claim 1, wherein the transmission imaging clock obtained by converting the master imaging clock comprises a transmission imaging clock obtained by multiplying the master imaging clock.

9. The electronic endoscopic apparatus according to claim 1, wherein the transmission imaging clock obtained by converting the master imaging clock comprises a transmission imaging clock obtained by dividing the master imaging clock.

10. The electronic endoscopic apparatus according to claim 1, wherein the transmission imaging clock obtained by converting the master imaging clock comprises a transmission imaging clock obtained by multiplying and dividing the master imaging clock.

* * * * *